United States Patent [19]

Barcelo et al.

[11] Patent Number: 4,891,430
[45] Date of Patent: Jan. 2, 1990

[54] PROCESS FOR SYNTHESIZING ACTIVE ESTERS OF CARBOXYLIC ACIDS, NEW ALPHA-HALOGENATED CARBONATES WHICH ARE USEFUL FOR THIS SYNTHESIS AND THE METHOD OF PRODUCING THEM

[75] Inventors: Gérard Barcelo, Sainte-Genevieve Des Bois; Bertrand Castro, Saint-Aunes, both of France; Mahmoud Jaouadi, G. de Sfax, Tunisia; Jean Martinez, Caux, France; Jean-Pierre Senet, La Chapelle La Reine, France; Gérard Sennyey, Gif Sur Yvette, France

[73] Assignee: Societe Internationale Des Poudres et Explosifs, Paris, France

[21] Appl. No.: 243,885

[22] Filed: Sep. 13, 1988

Related U.S. Application Data

[62] Division of Ser. No. 801,081, Nov. 22, 1985, Pat. No. 4,782,164.

[30] Foreign Application Priority Data

Dec. 4, 1984 [FR] France .................................. 84 18433

[51] Int. Cl.$^4$ ................ C07D 207/404; C07D 249/18
[52] U.S. Cl. .................................... 548/259; 548/475; 548/542; 558/270; 558/272
[58] Field of Search ................. 548/475, 542, 259; 558/270, 272

[56] References Cited

U.S. PATENT DOCUMENTS

| Re. 30,752 | 9/1981 | Itoh | 548/259 |
|---|---|---|---|
| 3,134,802 | 5/1964 | Gaertner | 558/270 |
| 3,598,856 | 8/1971 | Fujiwo | 558/270 |
| 3,835,175 | 10/1974 | Carpino | 558/270 |
| 4,282,151 | 8/1981 | Batz | 548/259 |
| 4,508,657 | 4/1985 | Carpino | 558/270 |
| 4,592,872 | 3/1986 | Cagnon et al. | 558/283 |
| 4,652,665 | 3/1987 | Barcelo et al. | 558/272 |
| 4,697,032 | 9/1987 | Malfroot et al. | 558/260 |

FOREIGN PATENT DOCUMENTS 0167451 1/1986 European Pat. Off.

OTHER PUBLICATIONS

Chem. Abst., vol. 107, 40326v, abstracting Fr 2,574,075.
Chem. Abstr., vol. 105, 60309d abstracting JP 61 43144.
Chem. Abst., vol. 104, 168201f abstracting EP 167451 (1986).
Chem Abst, vol. 105, 6403s, abstracting EP 165810.

*Primary Examiner*—Donald G. Daus
*Attorney, Agent, or Firm*—Bucknam and Archer

[57] ABSTRACT

The invention relates to a new process for preparing active esters or carboyxlic acids, which consists in reacting a carboxylic acid, in the presence of an agent for binding hydrohalic acid, with a carbonate of formula:

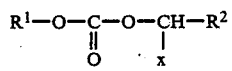

in which R$^1$ denotes either a radical of formula

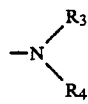

in which
R$^3$ and R$^4$, which may be identical or different, are not hydrogen atoms and denote organic radicals which may be substituted or unsubstituted and saturated or unsaturated, and may or may not be bound to a polymer, and which can be joined together to form a hetero-cyclic system with the nitrogen, atom,
or a substituted or unsubstituted aryl radical which may or may not be bound to a polymer,
R$^2$ denotes a hydrogen atom, an aliphatic or cycloaliphatic radical which may be substituted or unsubstituted and saturated or unsaturated, or a substituted or unsubstituted aromatic radical,
and X denotes a halogen atom.

This process is especially useful for the synthesis of active esters of N-protected amino acids. The invention also relates to the new carbonates described above and the method of producing them, which consists in reacting an alpha-halogenated chloroformate of formula:

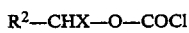

with an alcohol of formula R$^1$OH in an inert solvent medium in the presence of an organic or inorganic base.

13 Claims, No Drawings

PROCESS FOR SYNTHESIZING ACTIVE ESTERS OF CARBOXYLIC ACIDS, NEW ALPHA-HALOGENATED CARBONATES WHICH ARE USEFUL FOR THIS SYNTHESIS AND THE METHOD OF PRODUCING THEM

This application is a Divisional of U.S. Ser. No. 801,081, filed Nov. 22, 1985, which has issued as U.S. Pat. No. 4,782,164 on Nov. 1, 1988.

The invention relates to a new synthesis of active esters of carboxylic acids. It also relates to the new alpha-halogenated carbonates which are useful for this synthesis, and to the method of producing them.

Active esters of carboxylic acids are much sought after, especially in the field of peptide synthesis. Thus, esterified, N-protected amino acids are stable products which may be stored and marketed. It is subsequently only necessary to react them with an amino compound in order to form the peptide bond.

The various types of active esters are well described in the literature (Houben Weyl Vol. 15, 2nd part, or Specialist Periodical Reports "Amino-acides Peptides and Protein" Vol. 1–14).

Among the most common esters, substituted aryl esters, such as 2,4,5-trichlorophenyl esters, and esters of hydroxyamines, such as N-succinimidyl esters, may be mentioned.

These active esters can also be used for coupling biologically active molecules to proteins or to solid or liquid supports (German Patent Application No. 2,631,656, European Patent Application No. 2,677).

They are also used for grafting amino acids onto biologically active molecules (European Patent Applicationn No. 10,297).

A number of processes have already been proposed for preparing them [Tetrahedron 36 2409 (1980)].

The most widely used process consists in condensing the acid and the hydroxyl compound in the presence of dicyclohexylcarbodiimide as a dehydrating agent, but the yields are variable and there is formed, as by-product, dicyclohexylurea, which is very difficult to remove completely, and N-acylureas [Chem. Ber. 100, 16 (1967)].

According to another process, the hydroxylated compound is reacted with the mixed anhydride formed from the acid to be esterified and a carboxylic, carbonic or phosphoric acid chloride. Two stages are then generally necessary. Acid chlorides are unpleasant reagents to handle and are frequently toxic.

It is also possible to obtain active esters by reaction of the acid with a symmetrical carbonate formed from the hydroxylated compound. However, one equivalent of the hydroxylated compound is then lost, and this is frequently an expensive product which it is difficult to remove from the medium and recover.

It has also been proposed to replace the hydroxylated compound, in the case of 2,4-dinitrophenol, by its fluoride, which reacts with the sodium salt of the acid. However, this method is highly specific.

Some authors have, in fact, employed more sophisticated reagents such as 2-halopyridinium salts or the triphenylphosphine/diethyl azodicarboxylate system.

The very large number of processes proposed in the literature for producing these active esters tends to substantiate the view that none is entirely satisfactory, and that, in view of the value of these compounds, a better solution is still being sought.

The subject of the invention is specifically to propose a process in which this expectation is fulfilled.

According to the process of the invention, a carboxylic acid is reacted, in the presence of an agent for binding hydrohalic acid, with an alpha-halogenated carbonate of the formula

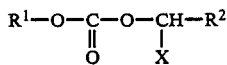

in which $R^1$ denotes either a radical of formula

in which $R^3$ and $R^4$, which may be identical or different, are not hydrogen atoms and denote highly diverse organic radicals which may be substituted or unsubstituted and saturated or unsaturated, and may or may not be bound to a polymer, and which can be joined together to form a heterocyclic system with the nitrogen atom, or a substituted or unsubstituted aryl radical which may or may not be bound to a polymer, $R^2$ denotes a hydrogen atom, an aliphatic or cycloaliphatic radical which may be substituted or unsubstituted and saturated or unsaturated, or a substituted or unsubstituted aromatic radical, and X denotes a halogen atom.

The reaction scheme is as follows:

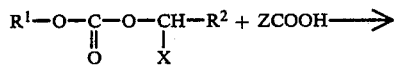

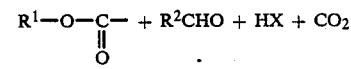

This reaction is surprising since, in effect, it is known that alpha-halogenated carbonates react with acids to give ester carbonates according to the scheme:

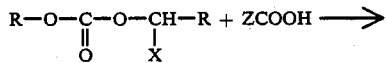

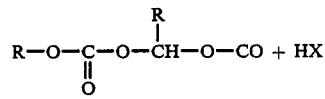

This reaction is described, in particular, in Patents FR 2,201,870 and EP 82,404, and is very useful for improving the efficacy of certain drugs.

The mechanism of the reaction according to the invention is completely different, and a merit of the invention is that the conditions have been discovered whereby active esters may be obtained.

The process according to the invention is applied to a very large number of simple or complex acids, saturated or unsaturated aliphatic, cycloaliphatic and heterocyclic acids, as well as aromatic acids. By way of example, acetic, acrylic, thiophenecarboxylic and benzoic acids may be mentioned.

It is especially useful for the esterification of N-protected natural or synthetic amino acids.

If the acids bear especially reactive groups, it is preferable to protect these but it is generally not necessary.

The alpha-halogenated carbonates of formula $$R^1-O-\underset{\underset{O}{\|}}{C}-O-\underset{\underset{X}{|}}{CH}-R^2$$

in which $R^1$ and $R^2$ have the above meanings and which are reacted with the acids, are new compounds which also form the subject of the present invention.

$R^3$ and $R^4$ can, for example, be aliphatic or aromatic radicals, and they are frequently joined together and $R^1$ then denotes one of a number of heterocyclic radicals. This heterocyclic system can comprise one or more hetero atoms which may be identical or different, and it can be saturated or unsaturated, may or may not be condensed with an aromatic system and can be substituted or unsubstituted.

$R^1$ also frequently denotes a substituted or unsubstituted phenyl radical.

The substituents of $R^1$ can be hydrocarbon groups, halogen atoms, especially chlorine or fluorine atoms, or functional groups such as nitro.

The radicals which are regarded as good activating groups in the active esters are the preferred radicals. These are, for example, N-succinimidyl, para-nitrophenyl, 2,4-dinitrophenyl, 2,4,5-trichlorophenyl, pentachloro or -fluorophenyl, and N-phthalimidyl radicals.

X is a halogen atom, a fluorine, chlorine, bromine or iodine atom, and is preferably chlorine.

$R^2$ generally denotes a $C_1$ to $C_5$ aliphatic radical, especially a methyl radical which can be substituted with one or more halogen atoms, or a phenyl radical which is unsubstituted or substituted with, for example, one or more halogen atoms.

The trichloromethyl radical is very suitable.

The alpha-halogenated carbonates of the invention are generally crystalline, stable at room temperature and of little or no toxicity.

The method of producing them, which also forms the subject of the invention, will be described shortly.

One of the applications thereof is the preparation of active esters as described above.

In this application, one equivalent of carbonate is generally used for one equivalent of acid. If necessary, it is possible to depart from this proportion.

The carbonate and the acid are reacted in a solvent which is inert with respect to them. This solvent is generally chosen from cyclic or acyclic ethers, such as tetrahydrofuran or dioxane, esters such as, for example, ethyl acetate, nitriles such as acetonitrile, alcohols such as, for example, isopropanol, amides such as, for example, dimethylformamide and ketones such as, for example, acetone. Tetrahydrofuran is very suitable.

The presence of an agent for binding hydrohalic acid is necessary, to remove the acid which forms during the reaction. All the customary means can be employed. This will generally be an inorganic base, for example potassium carbonate, of an organic base, for example a tertiary amine.

Among preferred bases, N-methylmorpholine or triethylamine may be mentioned.

One equivalent of base is generally used per equivalent of acid, but an excess of base is no disadvantage.

The reaction temperature is generally between $-20°$ and $100°$ C. It is chosen according to the reactivity of the carbonate used. It is most frequently between 20° and 30° C.

As regards the reaction time, this varies from a few minutes to a few hours. In general, two hours are sufficient to obtain good results. A simple means for establishing the completion of the reaction is to observe the cessation in the evolution of carbon dioxide.

The esterified acid obtained as purified by conventional, simple methods. The by-products of the reaction, which are the hydrochloride of the base used and the aldehyde, are readily removed, for example by washing with water. Then, by evaporation of the solvent, a product is obtained which is already of high purity and which can be recrystallised in a suitable solvent. The yields are excellent.

The invention also relates to the method of producing the new alpha-halogenated carbonates described above.

This method of production consists in reacting the hydroxylated compound of formula $R^1OH$, in which $R^1$ has the meaning given above, with an alpha-halogenated chloroformate of formula $$R^2-\underset{\underset{X}{|}}{CH}-O-\underset{\underset{O}{\|}}{C}-Cl$$

in which $R^2$ and X have the meaning given above, in an inert solvent medium at a temperature between $-20°$ and $100°$ C., in the presence of an organic or inorganic base.

The reaction is as follows:

$$R^1-OH + Cl-\underset{\underset{O}{\|}}{C}-O-\underset{\underset{X}{|}}{CH}-R^2 \longrightarrow$$

$$R^1-O-\underset{\underset{O}{\|}}{C}-O-\underset{\underset{X}{|}}{CH}-R^2 + HCl$$

The starting hydroxylated compounds and alpha-halogenated compounds are generally commercially available or are manufactured according to known methods. For example, the alpha-halogenated chloroformates are prepared by halogenation of the corresponding chloroformates, or as described in French Patent Applications Nos. 2,482,587 and 2,532,933, and European Patent Application 108,547.

As an organic or inorganic base, a base is generally employed which is known to bind hydrochloric acid. Pyridine or triethylamine is preferably used.

It is preferable to add the base to the mixture of the reagents, and also to add it gradually.

A stoichiometric amount of the base and the reactive components is generally used, but an excess of alcohol can be employed.

The solvent medium consists of one or more solvents which are inert towards the reagents. Chlorinated aliphatic solvents, for example dichloromethane and dichloroethane, cyclic or acyclic ethers, ketones such as acetone or 2-butanone, nitriles, esters and aliphatic or aromatic hydrocarbons are preferably chosen.

When certain hydroxylated compounds such as phenols are reacted, it is preferable to choose a solvent system in which the phenol is only slightly soluble and the hydrochloride of the base is insoluble. A benzene/petroleum ether mixture, for example, is very suitable.

The reaction temperature is preferably between −10° and 40° C.

When the introduction of the reagents is complete, the mixture is generally brought to room temperature. The reaction time is frequently between a few minutes and a few hours.

The carbonate obtained is readily isolated by the usual methods. For example, the mixture is washed with iced water or acid sodium sulphate, or filtered on a celite bed and the solvent or solvents then evaporated. The crystals generally obtained can be recrystallised in the conventional manner.

Thus, the invention enables new carbonates to be prepared in a simple manner without a special installation. Due to the originality of their structure, these new carbonates may form the subject of highly diverse applications.

The application to the esterification of acids, which also forms the subject of the present invention, is a very useful application. The active esters of the acids are thereby obtained without great difficulty and without racemisation, by using in a simple manner reagents which are easy to obtain and handle. The by-products of the reaction, the hydrochloride of the base used and aldehyde, are readily removed. The yields are very good and the products of high purity.

The examples which follow are given by way of illustration.

EXAMPLES 1 TO 10

Synthesis of alpha-halogenated carbonates

The carbonates are prepared according to one or more of the following methods. The results are collated in Table 1.

METHOD A 12.35 g (0.05 mol) of 1,2,2,2-tetrachloroethyl chloroformate are added in a single portion of a solution of 5.75 g (0.05 mol) of N-hydroxysuccinimide in dichloromethane (50 ml). The mixture is cooled to 0° C. and 4 g (0.05 mol) of pyridine is added dropwise. When the addition is complete, the mixture is allowed to return to room temperature and stirred for 3 hours. 20 ml of iced water are than added, and the organic phase is separated and washed with 20-ml portions of iced water as many times as are necessary until the pH is no longer acid (generally 3 to 4 times). The organic phase is dried over magnesium sulphate and evaporated, and a white solid is obtained which is crystallised in petroleum ether. 13.5 g (yield Y=83%) of the expected carbonate are collected. This recrystallisation can be obmitted; the yield is then 94% and the product is of satisfactory purity.

METHOD B

The procedure is as in Method A, replacing pyridine by triethylamine. The reaction is carried out for one hour at 0° C. and then one hour at room temperature. In this case, the organic phase is washed rapidly with saturated NaHSO4 solution. After evaporation, the N-hydroxysuccinimide carbonate is crystallised in ethyl ether (Y=83%).

METHOD C 27 g (0.11 mol) of 1,2,2,2-tetrachloroethylchloroformate are added to a suspension of 18.4 g (0.1 mol) of 2,4-dinitrophenol in 150 ml of benzene and 150 ml of petroleum ether. The mixture is cooled to 0° C. and 11 g (0.11 mol) of triethylamine are added dropwise while vigorous stirring is maintained. The mixture is stirred for 4 hours at 20° C. and then filtered on a celite bed. The solvents are evaporated and 26 g (Y=66%) of while crystals are obtained after being washed with a little petroleum ether.

TABLE 1

| Ex | Product | Method | Yield | Crystallisation solvent | M.p. or B.p. mm Hg °C. | $^1$H NMR ppm | IR cm$^{-1}$ | Elementary analysis |
|---|---|---|---|---|---|---|---|---|
| 1 | 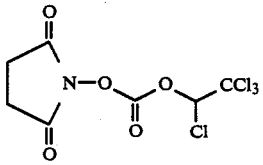 | A | 83 | Petroleum ether | 104 | 2,9 (s) 6,6 (s) | 1760 | C 26,000; H 1,74; N 4,10; O 23,54; Cl 43,55; (calculated: C 25,87; H 1,55; N 4,31; O 24,6; Cl 43,55; |
|   |   | B | 83 | Ethyl ether | 108 |   |   |   |
| 2 |   | A | 64 | Petroleum ether | 71 | 6,73 (s) 7,4 (s) | 1800 | C 26,61; H 1,02; O 11,56; Cl 60,80; (calculated C 26,54; H 0.74; O 11,78; Cl 60,93) |
| 3 |   | A | 92% crude 70% dist. | — | B.p. 0,02 150–155 | 6,7 (s) 7,4 (s) 7,56 (s) | 1795 | C 26,67; H 0,90; O 11,95; Cl 60,64; (calculated: C 26,54; H 0.74; O 11,78; Cl 60,93; |

TABLE 1-continued

| Ex | Product | Method | Yield | Crystal- lisation solvent | M.p. or B.p. mm Hg °C. | $^1$H NMR ppm | IR cm$^{-1}$ | Elementary analysis |
|---|---|---|---|---|---|---|---|---|
| 4 | 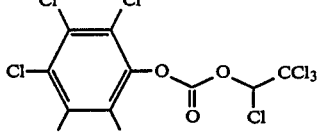 | A | 90 | AcOEt | 120 | 6,7 (s) | 1800 | C 22,40; H trace; Cl 67,15; (calculated: C 22,66; H 0,27; Cl 67,05 |
| 5 | 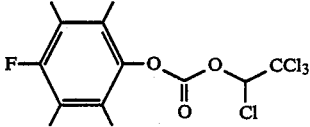 | A | 91 | — | B.p. 0,05 80 | 6,7 (s) | 1800 | C 27,60; H 0,47; Cl 35,80; F 24,56; (calculated 27,44; H 0,26; Cl 36,00; F 24,12); |
| 6 | 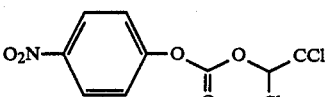 | C | 75 | Petrol- eum ether | B.p. 0,05 165 M.p. 69 | 6,7 (s) 7,5 (d) 8,36 (d) | 1790 | C 30,87; H 1.53; N 3,81; O 22,23; Cl 41,5 (calculated C 30,97; H 1,44; N 4,01; O 22.92; Cl 40,64) |
| 7 | 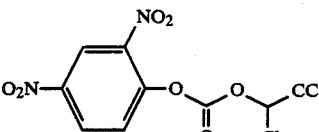 | C | 66 | Petrol- eum ether | 121–122 | 6,73 (s) 8,60 (s) 9,06 (d) 7,66 (d) | 1795 | C 27,49; H 1,04; N 6,98; O 27,99; Cl 35,95; (calculated C 27,44; H 1,02; N 7; O 28,43; Cl 36,00) |
| 8 | 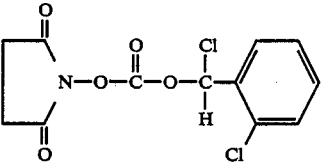 | A | 75 | | B.p. 0,05 115–131 | 2,8 (s) 7,2 (s) 7,3 to 8 (m) | 1750 | M$^+$ + 18 = 335 |
| 9 | 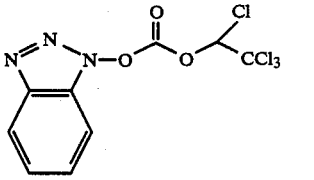 | B | 85 | CH$_2$Cl$_2$ | 145–147 | 7,04 (s) 7,6 (dd) 7,8 (dd) 8,0 (d) 8,2 (d) | 1770 1790 | C 31,38; H 1,37; N 12,16; Cl 41,03; calculated 31,30; H 1,45; N 12,17; Cl 41,16) |
| 10 | 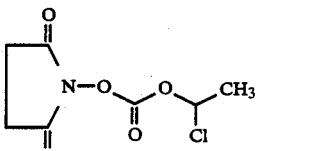 | A | 86 | Petrol- eum ether | 105–106 | 6,4 (q) 1,9 (d) 2,8 (s) | 1750 | C 37,80; H 3,64; N 6,24; O 36,68; Cl 15,88; calculated C 37,94; H 3,64; N 6,32; O 36,10; Cl 16,00 |

EXAMPLE 11

Preparation of N-succinimidyl N-tert-butyloxycarbonyl-L-alaninate 0.95 g (5 mmol) of N-tert-butyloxycarbonyl-L-alanine and 0.66 ml (5.5 mol) of N-methylmorpholine are dissolved in 6 ml of THF, and 1.8 g (5.5 mmol) of N-succinimidyl 1,2,2,2-tetrachloroethyl carbonate is added in a single portion. The mixture is stirred for two hours at 20° C. Approximately 25 ml of ethyl acetate are added and the organic phase is washed rapidly with NHCl solution, then with potassium bicarbonate solution and finally twice with water. The organic phase is dried over magnesium sulphate and evaporated. The residue is crystallised in an ethyl acetate/petroleum ether mixture and 1.25 g (Y=87%) of white crystals are obtained. Evaporation of the mother liquors and crystallisation enables a further 0.1 g to be recovered, and this brings the yield to 94%.

M.p. (melting point)=158° C.

$[\alpha]_D^{20}$=50.7 (c=2, dioxane)

EXAMPLE 12

Preparation of N-succinimidyl
Nα-tert-butyloxycarbonyl-Nε-benzyloxycarbonyl-L-lysinate 1.64 g (5 mmol) of N-succinimidyl 1,2,2,2-tetrachloroethyl carbonate is added to a solution of 1.9 g (5 mmol) of Nα-BOC-Nε-Z-lysine and 0.7 ml (5 mmol) of triethylamine in 15 ml of THF. The mixture is stirred at room temperature for 2 hours. 20 ml of ethyl acetate are then added and the organic phase is washed with 0.5N citric acid solution, then three times with 5% strength sodium bicarbonate solution and finally with saturated sodium chloride solution. The organic phase is dried over sodium sulphate and evaporated to dryness. 2.03 g (Y=85%) of white crystals are obtained.

M.p. 110° C.
$[\alpha]_D^{20} = -21.51$ (c=2, dioxane)
Analysis calculated for $C_{23}H_{34}N_3O_6.5H_2O$: C=56.79; H=6.79; N=8.64. Found C=56.32; H=6.44; N=8.77.

EXAMPLES 13 TO 29

Other N-succinimidyl esters are prepared as in Example 11 or 12. All the results are summarised in Table 2.

EXAMPLE 31

Preparation of N-succinimidyl N-tert-butyloxycarbonylglycinate

The procedure is as in Example 11, replacing THF by acetonitrile. Starting with 1.76 g of BOC-glycine, 2.1 g (Y=77%) of BOC-Gly-OSu is obtained.

M.p. 158° C.
M.p. Lit 168° C.

EXAMPLE 32

Preparation of N-succinimidyl N-tert-butyloxycarbonyl-N-phenylalaninate

To a solution of 1.33 g (5 mmol) of BOC-L-phenylalanine in 6 ml of THF, 0.66 ml of N-methylmorpholine and 1.11 g (5 mmol) of 1-chloroethyl N-succinimidyl carbonate are added. The mixture is stirred for 16 hours at 20° C. and treated as in Example 11. 1.40 g (Y=77%) of BOC-L-Phe-OSu is obtained.

M.p. 143° C.
$[\alpha]_D^{20} = -16.6$ (c=2,2 dioxane)

EXAMPLE 33

Preparation of (2-chlorophenyl)chloromethyl N-tert-butyloxycarbonyl-L-alaninate

TABLE 2

N—SUCCINIMIDYL ESTERS

| EX | Amino acid | Yield % | M.p. °C. | $[\alpha]_D^{20}$ (, solvent) | Literature yield % | M.p. °C. | $[\alpha]_D^{20}$ (c, solvent) | REF |
|----|------------|---------|----------|-------------------------------|--------------------|----------|---------------------------------|-----|
| 11 | BOC—Ala | 94 | 150 | −50,7 (2, dioxane) | 71 | 161 | −49,0 (2, dioxane) | 1 |
| 12 | BOC—(Z)—Lye | 85 | 110 | −21,51 (2, dioxane) | — | 110 | −21,12 (2, dioxane) | 2 |
| 13 | BOC—Phe | 91 | 147 | −19,8 (2, dioxane) | 81 | 152 | −20,7 (2, dioxane) | 1 |
| 14 | BOC—Gly | 91 | 162 | — | 62 | 168 | — | 1 |
| 15 | BOC—Val | 92 | 125 | −37,4 (2, dioxane) | 74 | 125 | −37 (2, dioxane) | 1 |
| 16 | BOC—Pro | 82 | 133 | −54,7 (2, dioxane) | 74 | 135 | −55,3 (2, dioxane) | 1 |
| 17 | BOC—Tyr | 69–74 | 181 | −12,12 (1, dioxane | | 180 | −12,5 (1, dioxane) | 2 |
| 18 | BOC—Trp | 89 | 140 | −23,13 (2, dioxane) | 37 | 153 | −22,4 (2, dioxane) | 1 |
| 19 | BOC—Met | 92 | 124 | −21,6 (2, dioxane) | 59 | 128 | −20,6 (2, dioxane) | 1 |
| 20 | BOC—(SBzl) Cys | 61 | 106 | −54,0 (2, dioxane) | 49 | 117 | −54,0 (2, dioxane) | 1 |
| 21 | BOC—(OBzl)—Ser | 78 | — | +5.8 (0,5, dioxane) | 52 | 112–113 | $-[\alpha]_D^{26}$ +6,5 (0,5 dioxane) | 2 |
| 22 | BOC—(OBzl)—Thr | 85 | — | +9,38 (2, dioxane) | — | 94 | −8,5 (1, methanol) | 2 |
| 23 | BOC—(OBzl) Tyr | 73 | 144 | −6,2 (2, dioxane) | — | 149 | −6,3 (2, dioxane) | 2 |
| 24 | z-Ala | 86 | 123 | −36,9 (2, dioxane) | 65 | 123 | −37,2 (2, dioxane) | 1 |
| 25 | z-Pro | 97 | 90 | −54,9 (2, dioxane) | 74 | 90 | −54 (2, dioxane) | 1 |
| 26 | z-Met | 72 | 102 | −16,2 (2, dioxane) | 59 | 102 | −15,9 (2, dioxane) | 1 |
| 27 | FMOC—Ala | 70 | 102 | — | — | — | — | — |
| 28 | FMOC—Phe | 97 | 137 | — | — | — | — | — |
| 29 | FMOC—Pro | 100 | — | — | — | — | — | — |

Ref. (1) J. Am. Chem. Soc. 86, 1839 (1964)
(2) Houben-Weyl: Methoden der Org. Chemie Vol. 15(2) p. 165 and loc. cit.

EXAMPLE 30

Preparation of N-succinimidyl N-tert-butyloxycarbonyl-N-phenylalaninate

To a solution of 1.33 g (5 mmol) of BOC-L-phenylalanine in 6 ml of THF, 0.8 g of anhydrous potassium carbonate and 1.8 g of 1,2,2,2-tetrachloroethyl N-succinimidyl carbonate are added. The mixture is stirred for two hours at 20° C. and treated as in Example 11. 1.15 g (Y=63%) of 80C-L-PheOSu is obtained. M.p. 135° C.

If 1 ml of aqueous potassium carbonate solution is used in place of anhydrous potassium carbonate, 1.3 g (Y=72%) of the above ester is obtained.

To a solution of 0.95 g (5 mmol) of BOC-L-alanine and 0.66 ml of N-methylmorpholine in 6 ml of THF, 2.0 g of (2-chlorophenyl)chloromethyl N-succinimidyl carbonate are added. The mixture is stirred for 1 hour 30 minutes at 20° C. and treated as in Example 11. 1.25 g (Y=90%) of BOC-L-Ala-OSu is obtained.

M.p. 158°–159° C.
$[\alpha]_D^{20} = -49.5$ (c=2, dioxane)

EXAMPLES 34 TO 42

Preparation of 2,4,5-trichlorophenyl esters

These esters are prepared as in Example 11 or 12, starting with 1,2,2,2-tetrachloroethyl 2,4,5-trichlorophenyl carbonate. The results are collated in Table 3.

EXAMPLE 43

Preparation of pentachlorophenyl
N-tert-butyloxycarbonyl-L-alaninate

The procedure is as in Example 12. Starting with 0.84 g (5 mmol) of BOC-L-alanine and 2.27 g (5 mmol) of pentachlorophenyl 1,2,2,2-tetrachloroethyl carbonate, 2.06 g (Y=94%) of white crystals are obtained (recrystallisation solvent: ethyl acetate/hexane).

M.p. 170° C.
$[\alpha]_D^{20} = -24.47$ (c=1, CHCl$_3$)
Literature:
M.p. 166° C.
$[\alpha]_D^{20} = -22.2$ (c=5.1, CHCl$_3$)

EXAMPLE 44

Preparation of pentachlorophenyl
N$^\alpha$-tertbutyloxycarbonyl-N$\epsilon$-benzyloxycarbonyl-L-lysinate The procedure is as in Example 12. Starting with 1.9 g of N$^\alpha$-BOC-N$\epsilon$-Z-L-lysine, 2.4 g (Y=77%) of N$^\alpha$-BOC-N$\epsilon$-Z-L-lysine-OPCP are obtained.

dried over magnesium sulphate. It is evaporated to dryness and the product is crystallised in 95% strength ethanol. 0.6 g (Y=62%) of white crystals are obtained.

M.p. 118° C.
$[\alpha]_D^{20} = -20.9$ (c=2, DMF)
literature:
M.p. 132° C. $[\alpha]_D^{20} = -21$ (c=2, DMF)

EXAMPLE 46

Preparation of 2,4-dinitrophenyl
N-tert-butyloxycarbonyl-L-alaninate

The procedure is as in the example above. Starting with 0.945 g (5 mmol) of N-BOC-L-alanine, 1.45 g (Y=82%) of N-BOC-L-Ala-O-2,4-DNP, crystallised in 95% strength ethyl alcohol, is obtained.

M.p. 95°-96° C.
$[\alpha]_D^{20} = -51.5$ (c=0.2, DMF)

EXAMPLE 47 TO 54

Preparations of pentafluorophenyl esters

The procedure is as in Example 11. The results are collated in Table 4.

TABLE 3
2,4,5-TRICHLOROPHENYL ESTERS

| EX | Amino acid | Yield % | M.p. °C. | $[\alpha]_D^{20}$ (c, solvent) | Literature yield | M.p. °C. | $[\alpha]_D^{20}$ (c, solvent) literature | Ref |
|---|---|---|---|---|---|---|---|---|
| 34 | BOC—Ala | 79 | 82 | −43,5 (2, acetic ac.) | 73 | 82 | −44 (2, acetic ac.) | 1 |
| 35 | BOC (SBzl) Cys | 60 | — | | 86 | 77 | — | 1 |
| 36 | BOC (DNP) Hist | 58 | 98 | +1,87 (2, dioxane) | — | — | — | |
| 37 | BOC—(OBzl) Glu | 60 | 107 | −33,5 (2, methanol) | 60 | 108 | −33,5 (2, methanol) | 2 |
| 38 | BOC—(Z) Lyn | 85 | 99 | −19,13 (2, dioxane) | 86 | 99 | — | 1 |
| 39 | BOC—Met | 79 | 90 | −38,0 (2, DMF) | 71 | 91 | −38,5 (2, DMF) | 1 |
| 40 | BOC—Ser | 22 | 105 | −42,0 (2, DMF) | 5 | 105 | −41 (2, DMF)) | 3 |
| 41 | BOC—(OBz-1) Ser | 77 | oil | +0,3 (2, dioxane) | — | — | — | — |
| 42 | BOC—Tyr. | 73 | 168 | −31,4 (3,5, acetic ac.) | 40 | 158 | −26,4 (3,5 acetic ac.) | 2 |

Ref. (1) J. Chem. Soc (C) (1967) - (2) Tetrahedron Suppl. 8,39 (1966) - (3) J. Med. Chem. 10, 1047 (1977)

TABLE 4
PENTAFLUOROPHENYL ESTERS

| EX | Amino acids | Yield % | M.p. °C. | Lit. M.p. °C. | $[\alpha]_D^{20}$ (c,solvent) | Literature $[\alpha]_D^{20}$ (c,solvent) | REF. |
|---|---|---|---|---|---|---|---|
| 47 | BOC—Ala | 90 | 85 | 83 | −34,6 (1, dioxane) | −31,2 (1, dioxane) | 1 |
| 48 | BOC—Gly | 90 | 80 | 80 | — | — | |
| 49 | BOC—Phe | 86 | 112 | 112 | −16,9 (1, dioxane) | −26,9 (1, dioxane) | 1 |
| 50 | BOC—Val | 94 | 64 | 64 | −31,8 (1, dioxane) | −18,4 (1, dioxane) | 1 |
| 51 | BOC—Pro | 98 | 50 | 51 | −48,2 (1, dioxane) | −53 (1, dioxane) | 1 |
| 52 | BOC—Trp | 91 | 111 | 111 | −12,8 (1, dioxane) | −28,1 (1, dioxane) | 1 |
| 53 | BOC—Met | 81 | 79 | 80 | −20,7 (1, dioxane) | −22,5 (1, dioxane) | 1 |
| 54 | z-Pro | 100 | oil | oil | −55,08 (1, dioxane) | −55,05 (1, dioxane) | 1 |

Ref. (1) Ann. 1421 (1973)

M.p. 142°
$[\alpha]_D^{20} = -16.7$ (c=1, CHCl$_3$)
Literature:
M.p. 141° C. $[\alpha]_D^{20} = -15.0$ (c=4.99, CHCl$_3$)

EXAMPLE 45

Preparation of 4-nitrophenyl
N-tert-butyloxycarbonyl-L-phenylalaninate 0.73 g (2.75 mmol) of BOC-L-phenylalanine and 0.3 ml of N-methylmorpholine are dissolved in 6 ml of THF, and 87 g (2.5 mmol) of 1,2,2,2-tetrachloroethyl 4-nitrophenyl carbonate are added. The mixture is stirred for one hour at room temperature. 15 ml of ethyl acetate are then added and the mixture is washed with normal hydrochloric acid solution and then with saturated sodium chloride solution. The orrganic phase is

EXAMPLE 55

Preparation of pentafluorophenyl
N-tert-butyloxycarbonyl-L-phenylalaninate

The procedure is as in Example 48, but varying the reaction solvent. The results obtained are collated in the following table:

| SOLVENT | YIELD | M.P.° C. | $[\alpha]^{20}$ |
|---|---|---|---|
| THF | 86 | 112 | −16.9 |
| DIOXANE | 86 | 113 | −16.4 |
| ETHYL ACETATE | 83 | 112 | −15.4 |
| DMF | 65 | 107 | −14.2 |

EXAMPLES 56 AND 57

These examples illustrate the use of the active esters of the amino acids in the synthesis of di- and tri-peptides.

56. Preparation of ethyl N-BOC-L-phenylalanylglycinate (BOC-Phe-Gly-OEt)

To a solution of 0.86 g (2 mmol) of pentafluorophenyl N-t-butyloxycarbonyl-L-phenylalaninate, prepared according to Example 48, in 10 ml of dioxane, 0.28 g (2.2 mmol) of ethyl glycinate (hydrochloride) and 0.31 g (3 mmol) of triethylamine are added simultaneously. The mixture is stirred for one hour at room temperature. It is diluted with 10 ml of ethyl acetate and washed with aqueous 0.1N hydrochloric acid, potassium bicarbonate and sodium chloride solutions. The organic phase is dried over magnesium sulphate and evaporation. The residue is taken up with a 4:6 ethyl acetate/hexane mixture and filtered on silica. After evaporation, 0.53 g (Y=76%) of BOC-Phe-Gly-OEt is obtained.

M.p. 89° C.
$[\alpha]_D^{20} = -4.8$ (c=5.0, EtOH)
M.P.$_{lit}$=89.5° C. $[\alpha]_D^{20} = -4.2$ (c=5.0, EtOH) [J. Amer. Chem. Soc. 82, 4596 (1960)]

57. Preparation of ethyl N-benzyloxycarbonylprolinylglycyl-glycinate

Z-Pro-GlyOH→Z-Pro-Gly-OPFP→Z-Pro-Gly-Gly-OEt 1.4 g (3.6 mmol) of 1,2,2,2-tetrachloroethyl pentafluorophenyl carbonate is added to a solution of 1.07 g (3.6 mmol) of N-benzyloxycarbonylprolinylglycine and 0.4 ml of N-methylmorpholine in 5 ml of dioxane. The mixture is stirred for one hour at 20° C. and treated as in Example 55.

0.82 g (Y=45%) of Z-Pro-Gly-OPFP is obtained:
$[\alpha]_D^{20} = -36.8$ (c=1, dioxane)

This 0.8 g is dissolved in 10 ml of dioxane, and 0.23 g (1.8 mmol) of ethyl glycinate hydrochloride and 0.25 g of triethylamine are added simultaneously. The procedure is then as in Example 55. 0.55 g (Y=94%) of Z-Pro-Gly-Gly-OEt is obtained.

M.p. 95°-96° C.
$[\alpha]_D^{20} = -21.4$ (c=1, EtOH)
which is recrystallised in an ethyl acetate/hexane mixture.
M.p. 117°-118° C.
$[\alpha]_D^{20} = -24.6$ (c=1, EtOH)
M.p.$_{lit}$ 120° C.
$[\alpha]_D^{20} = -26$ (c=1, EtOH)

EXAMPLE 58

Preparation of N-succinimidyl 2,2-dimethylacrylate 0.5 g of 2,2-dimethylacrylic acid in 15 ml of THF, 1.63 of 1,2,2,2-tetrachloroethyl N-succinimidyl carbonate and 0.7 ml of triethylamine are added. The mixture is stirred for 2 hours at 20° C. and washed with sodium chloride solution. The organic phase is dried over magnesium sulphate and the solvent is evaporated. 0.6 g (Y=56%) of the expected ester is obtained. $^1$H NMR (CDCl$_3$, TMS): 2.05 (s, CH$_3$); 2.2 (s, CH$_3$); 2.8 (s, CH$_2$CH$_2$); 5.9 (m, H—C≡).

EXAMPLE 59

Preparation of N-succinimidyl 2-thiophenecarboxylate

The procedure is as in the example above. Starting with 0.64 g of 2-thiophenecarboxylic acid, 0.62 g (Y=51%) of the expected ester is obtained.

M.p. 140°-142° C.
$^1$H NMR (CDCl$_3$, TMS): 2.8 (CH$_2$CH$_2$), 7.0–7.2 (m, H—C≡); 7.6 (m, H—C≡); 7.8 (m, H—C≡).

We claim:

1. An alpha-chlorinated carbonate of formula

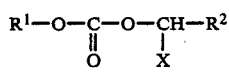

wherein R$^1$ is:
(1) N-succinimidyl;
(2) N-phthalimidyl;
(3) 1-benzotriazolyl;

R$^2$ is:
a saturated alkyl of 1 to 5 carbon atoms, unsubstituted or substituted by chlorine atoms, or an unsubstituted phenyl or phenyl substituted by chlorine atoms or wherein R$^1$ is phenyl substituted by 1–5 chlorine, fluorine or one or two nitro groups; and R$^2$ is a perchlorinated alkyl of 1 to 5 carbon atoms and X is chlorine.

2. A carbonate according to claim 1 wherein R$^1$ is N-succinimidyl, 2,4,5-trichlorophenyl, pentachloro- or pentafluorophenyl, 4-nitrophenyl, 2,4-dinitrophenyl or N-phthalimidyl.

3. A carbonate according to claim 1 wherein R$^2$ is trichloromethyl.

4. The carbonate accordiing to claim 2 which is:

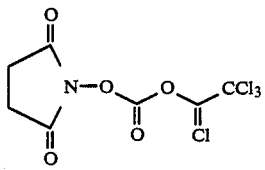

5. The carbonate according to claim 1 which is:

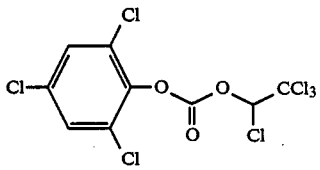

6. The carbonate according to claim 1 which is:

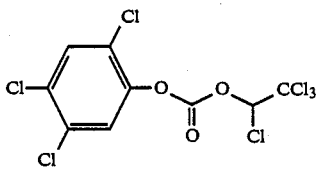

7. The carbonate according to claim 2 which is:

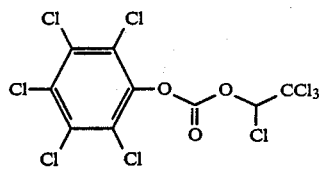
8. The carbonate according to claim 2 which is:
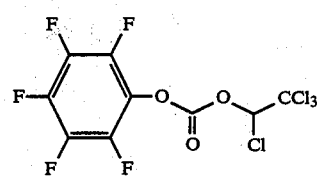
9. The carbonate according to claim 1 which is:
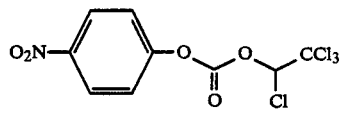
10. The carbonate according to claim 3 which is:
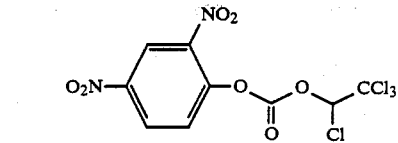
11. The carbonate according to claim 1 which is:
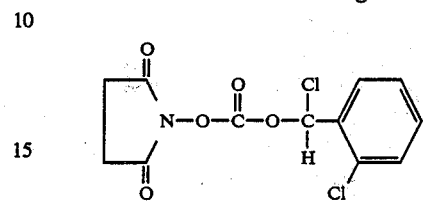
12. The carbonate according to claim 3 which is:
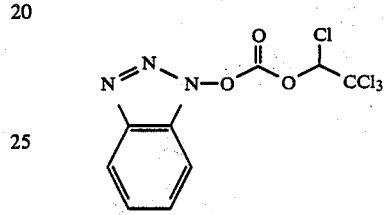
13. The carbonate according to claim 28 which is:
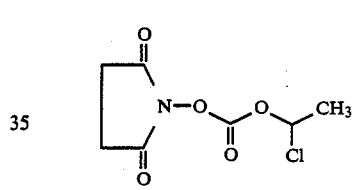
* * * * *